United States Patent
Roerdink et al.

(10) Patent No.: US 9,084,712 B2
(45) Date of Patent: Jul. 21, 2015

(54) DEVICE AND METHOD FOR DISPLAYING TARGET INDICATIONS FOR FOOT MOVEMENTS TO PERSONS WITH A WALKING DISORDER

(75) Inventors: Melvyn Roerdink, Amsterdam (NL); Peter Jan Beek, Amsterdam (NL)

(73) Assignee: FORCELINK B.V., Jr Culemborg (NL)

( * ) Notice: Subject to any disclaimer, the term of this patent is extended or adjusted under 35 U.S.C. 154(b) by 1581 days.

(21) Appl. No.: 12/415,059

(22) Filed: Mar. 31, 2009

(65) Prior Publication Data

US 2009/0246746 A1    Oct. 1, 2009

(30) Foreign Application Priority Data

Mar. 31, 2008  (NL) ...................................... 1035236

(51) Int. Cl.
*G09B 23/04* (2006.01)
*A61H 3/00* (2006.01)
*A63B 22/02* (2006.01)
*A61B 5/103* (2006.01)
*A63B 71/06* (2006.01)

(52) U.S. Cl.
CPC *A61H 3/00* (2013.01); *A63B 22/02* (2013.01); *A61B 5/1038* (2013.01); *A63B 22/0235* (2013.01); *A63B 2071/0694* (2013.01)

(58) Field of Classification Search
CPC . A63B 22/02; A63B 22/0235; A63B 69/0064
USPC ............. 600/595; 482/54; 435/255; 382/107; 340/524
See application file for complete search history.

(56) References Cited

U.S. PATENT DOCUMENTS

| 4,204,673 | A * | 5/1980 | Speer, Sr. ........................... 482/5 |
| 5,205,800 | A * | 4/1993 | Grant ............................... 482/54 |
| 6,152,854 | A * | 11/2000 | Carmein ........................... 482/4 |
| 6,438,255 | B1 * | 8/2002 | Lesniak ........................ 382/107 |
| 6,645,126 | B1 * | 11/2003 | Martin et al. ..................... 482/54 |

(Continued)

FOREIGN PATENT DOCUMENTS

| EP | 1 145 682 | 10/2001 | |
| EP | 1145682 A2 * | 10/2001 | ............... A61B 5/11 |

(Continued)

OTHER PUBLICATIONS

U.S. Appl. No. 11/910,417: Originally Filed Specification of Wolfson [filed Nov. 1, 2007] [retrieved Oct. 24, 2013].*

(Continued)

*Primary Examiner* — Robert J Utama
(74) *Attorney, Agent, or Firm* — Young & Thompson

(57) ABSTRACT

A walking-trainer device for persons with a walking disorder to relearn walking has a movable tread surface and a display unit for displaying target indications of the corresponding and consecutive foot positions for movements made by a person walking on the tread surface. The target indications have the form of a number of consecutive patterns located above a target surface at the height of and in the longitudinal direction of the tread surface moving in the direction of the person, which visibly move from a distance of between 0.5 m and 0.5 m, preferably between 15 m and 5 m and more preferably between 0.7 m and 2.5 m, from the target surface in the direction of and over the tread surface up to the feet of the person. The speed of movement of the patterns is substantially equal to the speed of movement of the tread surface.

20 Claims, 3 Drawing Sheets

(56) References Cited

U.S. PATENT DOCUMENTS

| | | | |
|---|---|---|---|
| 7,231,834 B2* | 6/2007 | Kurono | 73/800 |
| 7,540,828 B2* | 6/2009 | Watterson et al. | 482/54 |
| 7,628,732 B1* | 12/2009 | Porszasz et al. | 482/54 |
| 7,648,441 B2* | 1/2010 | Silk | 482/1 |
| 7,914,420 B2* | 3/2011 | Daly et al. | 482/9 |
| 8,257,232 B2* | 9/2012 | Albert | 482/69 |
| 2007/0255186 A1* | 11/2007 | Grill | 600/595 |
| 2007/0275830 A1* | 11/2007 | Lee et al. | 482/54 |
| 2008/0191864 A1* | 8/2008 | Wolfson | 340/524 |
| 2010/0152629 A1* | 6/2010 | Haas et al. | 601/34 |
| 2010/0285929 A1* | 11/2010 | Bayerlein et al. | 482/54 |
| 2011/0212810 A1* | 9/2011 | Jeka et al. | 482/9 |
| 2011/0312473 A1* | 12/2011 | Chu et al. | 482/54 |
| 2012/0021873 A1* | 1/2012 | Brunner | 482/9 |
| 2012/0178591 A1* | 7/2012 | Remelius | 482/54 |
| 2013/0060512 A1* | 3/2013 | Greene | 702/141 |
| 2013/0137553 A1* | 5/2013 | Kim et al. | 482/69 |
| 2013/0226048 A1* | 8/2013 | Unluhisarcikli et al. | 601/34 |
| 2014/0087922 A1* | 3/2014 | Bayerlein et al. | 482/54 |

FOREIGN PATENT DOCUMENTS

| | | |
|---|---|---|
| JP | 2003-164544 | 6/2003 |
| WO | 01/14018 | 3/2001 |

OTHER PUBLICATIONS

Netherlands Search Report dated Nov. 7, 2008, from corresponding Netherlands application.

* cited by examiner

DEVICE AND METHOD FOR DISPLAYING TARGET INDICATIONS FOR FOOT MOVEMENTS TO PERSONS WITH A WALKING DISORDER

There are various causes for the occurrence of a walking disorder in persons, which results in the loss of the ability to take regular steps whilst walking. These persons need to relearn the ability to walk in a regular manner by training. The invention relates to a walking device for training a person with a walking disorder, said walking device being provided with a movable tread surface and a display unit for displaying target indications of the corresponding and consecutive foot positions for movements made by persons walking on the tread surface. The invention also relates to a method for providing a series of consecutive target indications for the positions of foot movements of persons with a walking disorder walking on a treadmill.

A possible cause of a walking disorder can be a cerebral vascular accident (CVA) or stroke. Damage to parts of the brain and loss of certain brain functions occurs after a CVA. The may result in the loss of a person's ability to walk in a regular manner and symmetrically. It is known that by using a combination of sensory, tactile proprioscepsis (feedback of information from muscles, joints and ligaments) and balancing information, other parts of the brain may assume the functions of the damaged parts of the brain by training. Patients who need to learn how to walk again after a CVA are required to learn this by observation, interpretation and by trial and error. In doing so, it is therefore desirable to provide, as soon as possible, a large amount of direct sensory input within a safe environment that retrains the brain to generate correct impulses in order to be able to walk in a regular manner.

A walking-trainer device to train persons with a walking disability on a treadmill is known from EP 1 145 682. In order to achieve a desired walking rhythm and step length, step indications are displayed to a person placed on a moving treadmill via a monitor placed opposite the person. The step length is determined by the duration between two consecutive step indications. Using a force sensor to determine the stepping moments, the step length and step frequency can be measured and the belt speed can be adjusted to the steps. By adjusting the belt speed to the step cycle of the patient and to his ideal, desired step length, a neurologic impulse is generated in the patient which effectuates a normal step pattern with the corresponding correct step length. Patients can thereby relearn subconsciously to walk symmetrically by repetition. The known device has the disadvantage that the reality is only partially reflected by the use of the display unit. This means that head movements, for example, and observations from the corner of the eyes, which provide important information in regular walking, are of no influence (to the training process). Furthermore, the known device is based on a predetermined ideal step length in order to control the belt speed, which could result in the fact that the walking exercise does not optimally reflect the actual walking ability of the person with a disorder at any given moment.

Another training device for training patients suffering from Parkinson's disease is known from JP2003164544 and includes a walker on which a display is mounted, and a number of light elements above the tread surface, so that lines of light can be projected as target indications in front of the patient's feet. Because the patient supports himself with his arms on the walker whilst walking, the walking pattern changes and so natural walking is only reflected to a limited degree. In addition, pushing the walker causes inconsistencies in the learning process. Furthermore, the vision of the patient is restricted whilst walking by the screen placed in front of him, a relatively large amount of space is required to provide the patient with the required freedom of movement and the patient is not easily observed by the therapist.

It is an object of the invention to provide a device and method for providing target indications for foot movements of persons with a walking disorder, wherein the actual walking situation is simulated as accurately as possible. It is also an object of the invention to provide a device and method wherein the movements of the head and eyes of the person walking contribute to the learning process. It is an additional object to provide a device and method by which a walking pattern can be learned in a quick, safe and comfortable manner by persons with a walking disorder.

To achieve this, the device according to the invention is characterized in that the target indications have the form of a number of consecutive patterns (15, 16) located above a target surface (10) at the height of and in the longitudinal direction of the tread surface moving in the direction of the person, which, from a distance of between 0.5 m and 10 m, preferably between 0.5 and 5 m, with even greater preference between 0.7 m and 2.5, visibly move from the target surface (10) up to and over the tread surface (3) and up to the feet of the person (4), wherein the speed of movement of the patterns (15, 16) is substantially equal to the speed of movement of the tread surface (3).

The person walking over the tread surface sees a moving pattern, preferably a zebra pattern of illuminated lines at a relatively large distance, coming towards him and can therefore anticipate the position in which he will place his feet on or between said pattern. The pattern of lines moving towards the person with the speed of the belt via the target surface and the tread surface can be used to achieve a natural effect and so also enable the person to process information originating from head movements and from sensory input obtained by a natural and spatial observation. It is anticipated that it is possible, in this manner, to relearn a regular walking pattern very quickly. Because the person standing on the treadmill does not move in the spatial environment, the walking exercises can be performed with the device according to the invention on a relatively small surface, thus enabling close observation by a therapist.

The tread surface of the device according to the invention can be an actively or passively driven treadmill. By constructing this treadmill relatively long, the tread surface can be formed by the treadmill portion which extends in front of the person. On the other hand, the target surface may also be static and may comprise a horizontal plate extending in the longitudinal direction of the treadmill. The belts moving over the target surface can be projected onto the target surface by a projection means, from an upper side or from a lower side of the surface. It is also possible for the target surface to be provided with active light elements such as LEDs, or that the pattern is projected onto the target surface by laser means.

The number of belts that a persons sees projected in front of him depends on the length of the projection surface extending in front of the person, the belt speed and step frequency. The width (W) of the belts is adjustable from a line to an area in which the foot fits, depending on the therapeutic objective of the therapist.

In one embodiment the number of belts amounts to between 1 and 20, preferably between 3 and 15, wherein the belts have a width, in the direction of movement, of between 10 and 50 cm, preferably between 1 and 40 cm.

Because the person with a walking disability can anticipate the step to be taken based on the approaching light belts, a positive learning effect may be achieved. Furthermore, the width of the belts is preferably relatively large so that the person will not easily miss the belt when deviations in the step length occur.

In a preferred embodiment, the tread surface is equipped with sensors for measuring a unit of force exerted by the person on the tread surface as he walks.

The signal from the sensors can be fed to a control unit, which then calculates a position of the centre of gravity of a person walking on the tread surface, whereby the position of the centre of gravity is fed to a display unit in order to be displayed in relation to the person walking.

By displaying the position of the centre of gravity, either by means of projection onto the tread surface, or by display on a monitor, the therapist can intervene and adjust the relative distance of the light belts in order to eliminate asymmetry in the walking pattern. Furthermore, if the person performing the exercise lags behind, this can be detected by determining the centre of pressure in relation to the belt and the belt speed can be decreased.

The method for providing target indications to a person on a treadmill according to the invention comprises the steps of:
measuring the foot positions of the person on said treadmill by sensor means,
determining the speed of the treadmill,
feeding the sensor signals to a control unit and determining the step frequency or step length, and
displaying a number of consecutive belts located above a target surface at the height of and in the longitudinal direction of the tread surface moving in the direction of the person, which visibly move in the direction of the person from a distance of between 0.5 m and 10 m, preferably between 0.5 m and 5 m, more preferably between 0.7 m and 2.5 m, from the target surface up to and over the tread surface, the belt speed of which corresponds substantially to the speed of the treadmill.

After the belt pattern has been adjusted by the control unit to the natural step length of the person by processing the sensor signals and belt speed, the therapist can intervene by adjusting the individual distance of the lines. This can be done simply by operating the arrow keys for more (up) or less (down) symmetry, or by using a "drag bar" whereby the length of two bars on a display show the degree of asymmetry in the steps, or by an algorithm which, for example, adjusts the symmetry from 15% to 5% in an N number of steps.

With regard to the numerical indication of asymmetry in terms of step length and step time, it is preferable for the symmetry to be determined by displaying the contour of the centre of gravity of the person whilst walking. As will be set forth in a detailed description of the accompanying figures, this has the shape of a butterfly, thus enabling the therapist to adjust the step parameters quickly and intuitively.

A device and method according to the invention will now be described in greater detail with reference to the accompanying drawing. In the drawing:

FIG. 1 shows a schematic view of a walking-trainer device according to the invention, FIG. 2 shows a top view of the device according to FIG. 1, FIG. 3 shows a butterfly-shaped contour of the centre of gravity, and FIG. 4 shows a typical belt pattern for compensating asymmetry in the step, and FIG. 5 shows a schematic representation of the pattern of belts by the control unit.

FIG. 1 shows a training device 1 for persons with a walking disorder to relearn to walk symmetrically. The training device 1 comprises a treadmill 2 which is driven by a motor 6. The treadmill 2 has a tread surface 3 on which the person 4 walks. A number of sensors 5 are located beneath the tread surface 3, which are connected with a control unit 7. A target surface 10 is located in the longitudinal direction of the treadmill 2 which, as far as height and appearance are concerned, connects seamlessly with the tread surface. A number of projectors 8, 9 are mounted above the target surface 10 which project a pattern of consecutive belts onto the target surface 10 and onto the tread surface 3, such that these belts move with a speed Vb, which is equal to the treadmill belt speed Vl in the direction of the person 4.

In an alternative embodiment, the target surface 10 is formed by the extension of the treadmill 2 which, in this case, extends a relatively large distance in front of the person.

The projectors 8, 9 are connected to the control unit 7, which can control the width W of the light belts, the speed Vb over the target surface 10 and the tread surface 3, and the individual distance between the light belts. In addition, the motor 6 is connected to the control unit 7 for determining and adjusting the speed Vl of the treadmill. The control unit 7 is connected via an output to a monitor 12 for displaying walking pattern parameters such as the step length and step frequency of the person 4 and the position of the centre of gravity Cg of the person, which is calculated on the basis of the signals produced by the sensors 5. The therapist can adjust the speed of the treadmill 2 using a keyboard 13, and, accordingly, adjust the pattern of light belts (V speed, distance and width).

A projector 14 can be used to project the position of the centre of gravity Cg of the person 4 on the treadmill 2 calculated by the control unit 7. It is also possible for the projectors 8, 9 and 14 to be implemented as an integrated projector unit.

FIG. 2 shows a top view of the tread surface 3 and the target surface 10. The light belts 15, 16 have, for example, a width W of 20 cm and a lateral dimension D of 50 cm. The individual distance $\Delta_l$, $\Delta_r$ is, for example, in the absence of asymmetry, 70 cm and the speed Vb in the direction of the person 4 is, for example, 1.5 m/s. The length L1 of the target surface 10 and the length L2 of the portion of the tread surface 3 extending in front of the person, and onto which the light belts 15, 16 are projected is, for example, 3 m. The number of light belts 15, 16 is, for example, 4 belts.

The symmetry of the walking pattern of the person 4 can be manipulated by adjusting the individual distance $\Delta_l$, $\Delta_r$ between two light belts by the therapist. If the person 4 shows an asymmetric walking after suffering from a CVA, for example, the person can be trained to develop a more symmetrical walking pattern by varying the distance $\Delta_l$, $\Delta_r$ between the light belts. To achieve this, the therapist adjusts the individual distance $\Delta_l$, $\Delta_r$ between the light belts via the keyboard (or other input device, such as a light pen or voice-activated command).

FIG. 3 shows the image on the monitor 12 of the locus of the center of gravity Cg of the person 4 on the tread surface 3. During the standing phase of the left leg, whilst the foot is placed on the treadmill, the Cg moves backwards along the path B-A until the right foot lands on the treadmill (A). During this so-called 'double-support phase', in which both feet are placed on the treadmill, the Cg moves from point A in the direction of point E, which is reached once the left foot leaves the ground. During the subsequent standing phase of the right leg, the Cg moves backwards together with the foot along the path E-D until the left foot is placed (point D) on the treadmill again. During the double-support phase (path D-B), the Cg moves to the front left position until the right foot is lifted from the treadmill (point B). In this manner, the locus of the centre of gravity forms a butterfly shaped figure, the symmetry of which is a direct visual measure of the symmetry of the steps taken by the person 4. This butterfly figure, which is displayed on the monitor 12, can be used by the therapist to quickly and effectively adjust the distance Δ l, Δ r between the light belts to obtain a symmetrical pattern.

Figure 1:
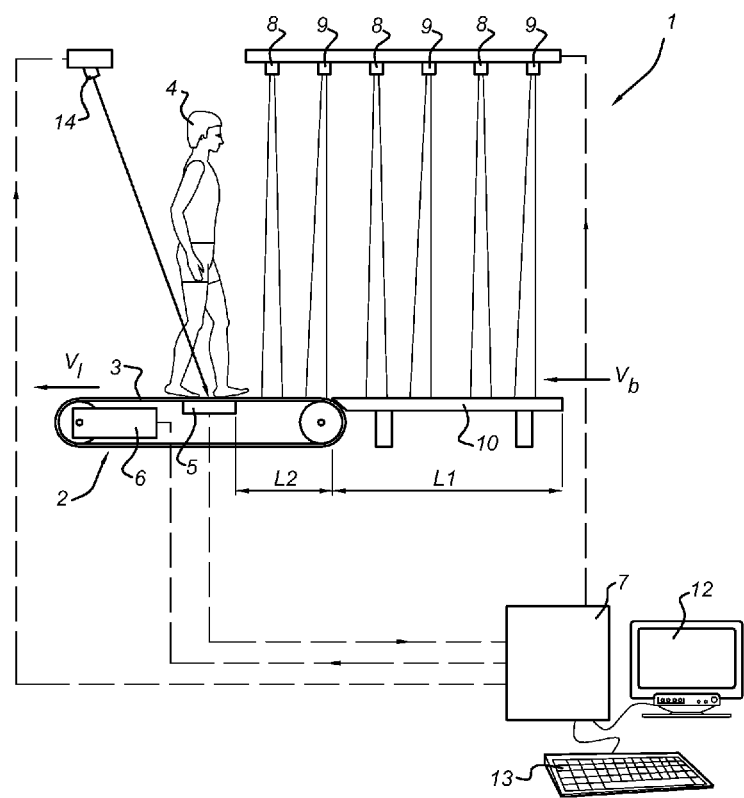
Figure 2:
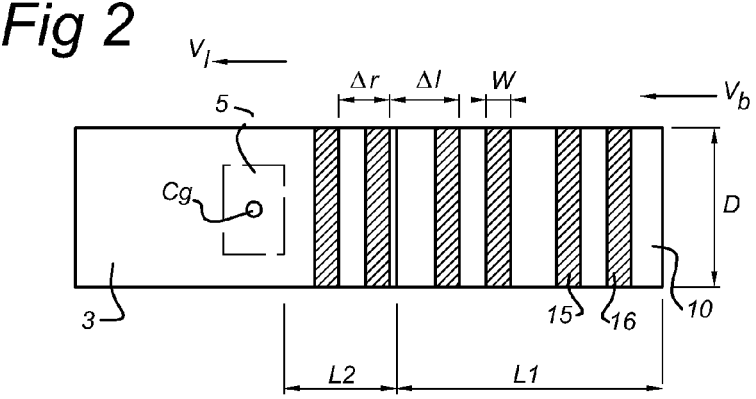
Figure 3:
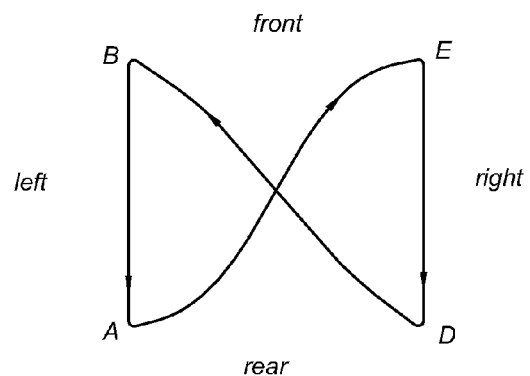
Figure 4:
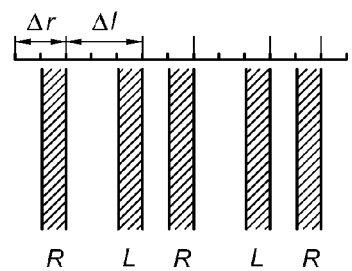
FIG. 4 shows a typical pattern of left (L) and right (R) hand light belts for a person with an asymmetrical walking pattern ($\Delta_l$=60 cm, $\Delta_r$=40 cm).
Figure 5:
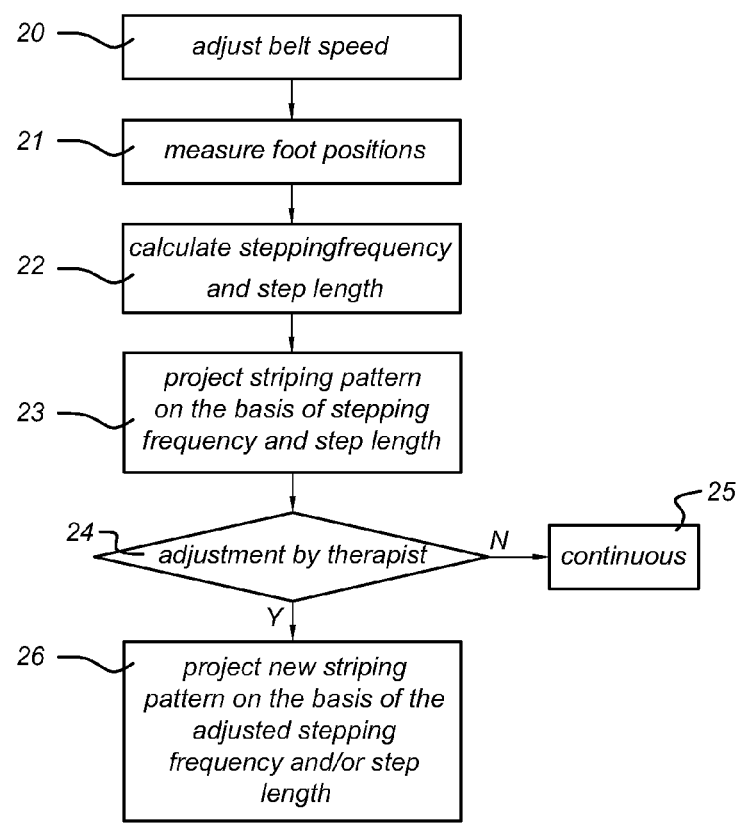
FIG. 5 shows a schematic diagram of how the pattern of the light belts is determined in the control unit 7.

In step 20, the belt speed of the treadmill 2 is adjusted, for example, by the therapist using the keyboard 13. Subsequently, in step 21 the foot positions are measured via the sensors 5 and the step frequency and step lengths Δl, Δr are determined in step 22.

Based on the left step length and right step length and the step frequency, in step 23 the light belts are projected onto the target surface 10 and tread surface 3, whereby the speed of the belts Vb corresponds to the treadmill speed Vl and the distances Δ l, Δ r correspond to the step lengths of the right step and left step. After intervention by the therapist (step 24), the relative distances $\Delta_l$, $\Delta_r$ are immediately adjusted (step 26), so that, for example, a change in the symmetry or step frequency of the person can be achieved.

The invention claimed is:

1. A walking-trainer device (1), comprising:
   a movable tread surface; and
   an indicator unit (7, 8, 9) for displaying consecutive target indications on the tread surface, the target indications corresponding to positions on the tread surface (3) for foot placement of a person (4) walking on said tread surface,
   wherein the target indications have the form of a plurality of consecutive patterns (15, 16) located on the tread surface and a target surface (10) at the height of and in a longitudinal direction of the tread surface,
   the indicator unit configured to move the target indications from the target surface (10) in a direction of the person, wherein the pattern, from a distance of between 0.5 m and 10 m (19.7 inches and 393.7 inches), visibly moves from the target surface (10) in a direction of and over the tread surface (3) and up to the feet of the person (4), a speed of movement of the patterns (15, 16) being substantially equal to a speed of movement of the tread surface (3).

2. The walking-trainer device (1) according to claim 1, wherein the patterns comprise a number of lines (15, 16), a number of which lies between 1 and 20, each line having a width W of between 1 and 50 cm (0.39 and 19.68 inches) measured in the direction of movement.

3. The walking-trainer device (1) according to claim 1,
   wherein the target surface (10) has a length (L1) of between 0.5 m and 10 m (19.7 inches and 393.7 inches), and
   wherein the target surface is stationary.

4. The walking-trainer device (1) according to claim 1,
   wherein the tread surface (3) is provided with sensors (5) for determining the path of the centre of gravity and foot positions on said tread surface,
   wherein the sensors (5) produce a signal which is fed to a control unit (7) which calculates a position of the centre of gravity of a person (4) walking on the treadmill, and
   wherein the position of the centre of gravity is fed to a display unit (12, 14) in order to be displayed in relation to the person walking.

5. The walking-trainer device (1) according to claim 4, wherein the centre of gravity is projected by a projector (8, 9, 14) onto said tread surface.

6. The walking-trainer device (1) according to claim 3, wherein the signal from the sensors (5) is fed to a control unit (7) in order to control the speed of movement and/or the individual distance of the paths (16, 17).

7. A method for displaying target indications to a person walking on a treadmill, comprising the steps of:
   measuring, via sensors, the foot positions of the person on said treadmill;
   determining the speed of the treadmill;
   feeding the sensor signals to a control unit and determining at least one of a step frequency of the person and a step length of the person; and
   displaying a plurality of consecutive lines on a tread surface of the treadmill and on a target surface that is at a height of and in a longitudinal direction of the tread surface, the consecutive lines visibly moving in a direction of the person from a distance of between 0.5 m and 10 m (19.7 inches and 393.7 inches) from the target surface in a direction of and over the tread surface, a speed of the consecutive lines corresponding substantially to a speed of the tread surface of the treadmill.

8. The method according to claim 7, wherein a distance between consecutive lines is adjusted on the basis of the step frequency and/or the step length.

9. The method according to claim 8, wherein a centre of gravity position, based on sensor signals of the person, is displayed in the form of a butterfly-shaped representation on a display unit.

10. The method according to claim 7, wherein the display of the lines is set in such a manner that positions between two lines are located beneath the feet of the person.

11. The method according to claim 8, wherein the display of the lines is set in such a manner that positions between two lines are located beneath the feet of the person.

12. The method according to claim 9, wherein the display of the lines is set in such a manner that positions between two lines are located beneath the feet of the person.

13. The walking-trainer device (1) according to claim 2,
   wherein the target surface (10) has a length (L1) of between 0.5 m and 10 m (19.7 inches and 393.7 inches), and
   wherein the target surface is stationary.

14. The walking-trainer device (1) according to claim 2,
   wherein the tread surface (3) is provided with sensors (5) for determining the path of the centre of gravity and foot positions on said tread surface,
   wherein the sensors (5) produce a signal which is fed to a control unit (7) which calculates a position of the centre of gravity of a person (4) walking on the treadmill, and
   wherein the position of the centre of gravity is fed to a display unit (12, 14) in order to be displayed in relation to the person walking.

15. The walking-trainer device (1) according to claim 3,
   wherein the tread surface (3) is provided with sensors (5) for determining the path of the centre of gravity and foot positions on said tread surface,
   wherein the sensors (5) produce a signal which is fed to a control unit (7) which calculates a position of the centre of gravity of a person (4) walking on the treadmill, and
   wherein the position of the centre of gravity is fed to a display unit (12, 14) in order to be displayed in relation to the person walking.

16. The walking-trainer device (1) according to claim 1, wherein the pattern from a distance between 0.5 m (19.7 inches) and 5 m (196.8 inches) visibly moves from the target surface (10) in the direction of and over the tread surface (3) up to the feet of the person (4).

17. The walking-trainer device (1) according to claim 1, wherein the pattern from a distance between 0.7 m (27.6 inches) and 2.5 m (98.4 inches) visibly moves from the target surface (10) in the direction of and over the tread surface (3) up to the feet of the person (4).

18. The walking-trainer device (1) according to claim 2, wherein the number of lines is between 3 and 15, and the width W of each of the lines is between 1 cm and 40 cm (0.39 and 15.75 inches).

19. The method according to claim 7, wherein the consecutive lines visibly move in the direction of the person from a distance of between 0.7 m (27.6 inches) and 2.5 m (98.4 inches).

20. A walking-trainer device (1), comprising:

a treadmill (2), with a movable tread surface (3) and a target surface (10) located at a front end of the tread surface (3) and extending in a longitudinal direction of the tread surface (3) and co-planar with the tread surface (3); and an indicator unit (7, 8, 9) that displays consecutive visible target indications on the tread surface (3), the indicator unit configured to display the target indications at locations on the tread surface (3) corresponding to positions on the tread surface (3) of foot placement of a person (4) walking on said tread surface (3), wherein the target indications have the form of a plurality of consecutive patterns (15, 16) that visibly run along a length of the target surface (10) and the tread surface (3), the indicator unit configured to cause the patterns (15, 16) to visibly move from the target surface (10) to the tread surface (3) in a direction of the person (4) walking on the tread surface (3), a speed of movement of the patterns (15, 16) being substantially equal to a speed of movement of the tread surface (3).

\* \* \* \* \*